(12) United States Patent
Herskovic

(10) Patent No.: US 10,238,891 B2
(45) Date of Patent: Mar. 26, 2019

(54) DEVICE AND METHOD FOR IMPROVING BRACHYTHERAPY

(71) Applicant: BOSTON SCIENTIFIC CORPORATION, Natick, MA (US)

(72) Inventor: Arnold M. Herskovic, Chicago, IL (US)

(73) Assignee: BOSTON SCIENTIFIC CORPORATION, Marlborough, MA (US)

(*) Notice: Subject to any disclaimer, the term of this patent is extended or adjusted under 35 U.S.C. 154(b) by 28 days.

(21) Appl. No.: 14/629,067

(22) Filed: Feb. 23, 2015

(65) Prior Publication Data

US 2015/0190654 A1 Jul. 9, 2015

Related U.S. Application Data

(63) Continuation of application No. PCT/CN2013/056373, filed on Aug. 23, 2013.

(Continued)

(51) Int. Cl.
*A61N 5/10* (2006.01)

(52) U.S. Cl.
CPC .......... *A61N 5/1007* (2013.01); *A61N 5/1001* (2013.01); *A61N 5/1002* (2013.01);
(Continued)

(58) Field of Classification Search
CPC ...... A61N 5/10; A61N 5/1001; A61N 5/1002; A61N 5/1007; A61N 5/1014–5/1017; A61N 5/1027; A61N 2005/1003–2005/1005; A61N 2005/1008–2005/1012; A61N 2005/1018–2005/1025
See application file for complete search history.

(56) References Cited

U.S. PATENT DOCUMENTS

| 5,713,828 A | 2/1998 | Coniglione |
| 5,891,108 A | 4/1999 | Leone et al. |

(Continued)

FOREIGN PATENT DOCUMENTS

| WO | 02049535 A2 | 6/2002 |
| WO | 03037397 A2 | 5/2003 |
| WO | 2007082189 A2 | 7/2007 |

OTHER PUBLICATIONS

Gaspar, et al., "American Brachytherapy Society (ABS) Consensus Guidlines for Brachytherapy of Esophageal Cancer", INT. J. Radiation Oncology Biol. Phys., vol. 38, No. 1, pp. 127-132, 1997.

(Continued)

*Primary Examiner* — Thaddeus Cox
(74) *Attorney, Agent, or Firm* — Seager, Tufte & Wickhem, LLP

(57) ABSTRACT

This invention is a medicament delivery vehicle, the vehicle comprising tubular members adapted to removably receive the medicament and an expandable stent adapted to receive the tubular members. Also provided is a medicament delivery vehicle, the vehicle comprised of tubular members which receive the medicament wherein the medicament comprises discrete entities and each of said entities are removably positioned at predetermined regions within the members.

19 Claims, 5 Drawing Sheets

Related U.S. Application Data

(60) Provisional application No. 61/692,802, filed on Aug. 24, 2012.

(52) U.S. Cl.
CPC .......... *A61N 5/1014* (2013.01); *A61N 5/1027* (2013.01); *A61N 2005/101* (2013.01); *A61N 2005/1004* (2013.01); *A61N 2005/1005* (2013.01); *A61N 2005/1008* (2013.01); *A61N 2005/1018* (2013.01); *A61N 2005/1023* (2013.01)

(56) References Cited

U.S. PATENT DOCUMENTS

| | | | |
|---|---|---|---|
| 6,159,143 A | 12/2000 | Lennox | |
| 6,192,271 B1* | 2/2001 | Hayman | A61N 5/1002 604/21 |
| 6,402,736 B1* | 6/2002 | Brown | A61M 25/0017 604/264 |
| 6,524,232 B1 | 2/2003 | Tang et al. | |
| 6,537,193 B1 | 3/2003 | Lennox | |
| 6,569,076 B1* | 5/2003 | Larsen | A61N 5/1002 600/3 |
| 6,582,353 B1 | 6/2003 | Hastings et al. | |
| 6,599,230 B2 | 7/2003 | Hastings et al. | |
| 6,638,205 B1 | 10/2003 | Chan et al. | |
| 6,716,156 B2 | 4/2004 | Menuhr et al. | |
| 6,918,869 B2 | 7/2005 | Shaw et al. | |
| 7,074,291 B2 | 7/2006 | Terwilliger et al. | |
| 7,252,630 B2 | 8/2007 | Terwilliger et al. | |
| 7,344,490 B2 | 3/2008 | Shaw et al. | |
| 7,351,192 B2 | 4/2008 | Elliott et al. | |
| 7,887,476 B2 | 2/2011 | Hermann et al. | |
| 8,114,007 B2 | 2/2012 | Lamoureux et al. | |
| 8,298,129 B2 | 10/2012 | Elliott et al. | |
| 2001/0001112 A1 | 5/2001 | Hayman | |
| 2002/0133220 A1* | 9/2002 | Lundqvist | A61K 41/009 623/1.15 |
| 2002/0193655 A1 | 12/2002 | Candelaria et al. | |
| 2004/0116767 A1* | 6/2004 | Lebovic | A61N 5/1027 600/7 |
| 2004/0225176 A1* | 11/2004 | Flanagan | A61N 5/1007 600/7 |
| 2007/0225795 A1* | 9/2007 | Granada | A61F 2/91 623/1.15 |
| 2007/0270627 A1* | 11/2007 | Cutrer | A61N 5/1015 600/7 |
| 2008/0071132 A1 | 3/2008 | Lamoureux et al. | |
| 2009/0076588 A1* | 3/2009 | Weber | A61F 2/90 623/1.15 |
| 2009/0093668 A1 | 4/2009 | Marten et al. | |
| 2009/0326314 A1 | 12/2009 | Cutrer et al. | |
| 2010/0030127 A1* | 2/2010 | Liu | A61F 2/04 604/8 |
| 2010/0152833 A1* | 6/2010 | Burnside | A61F 2/07 623/1.13 |

OTHER PUBLICATIONS

Talreja, et al., "Fully covered removable nitinol self-expandable metal stents (SEMS) in malignant strictures of the esophagus: a multicenter analysis", Surg. Endosc. (2012) 26:164-1669.

Lendlein, et al., "Shape-Memory Polymers", Angew. Chem. Int. Ed. 2002, 41, 2034-2057.

Langley, et al., "4D Brachytherapy, a novel real-time prostate brachytherapy technique using stranded and loose seeds", BJU International, 2012, 109, Supplement 1, 1-9.

* cited by examiner

DEVICE AND METHOD FOR IMPROVING BRACHYTHERAPY

CROSS-REFERENCE TO RELATED APPLICATIONS

This application is a continuation of PCT Application No. PCT/US2013/056373, filed Aug. 23, 2013 which claims priority to U.S. Provisional Application Ser. No. 61/692,802, filed Aug. 24, 2012, the entire disclosures of which are incorporated herein by reference.

FIELD OF THE INVENTION

The present invention relates to a device and method for delivering medicaments and more particularly, the present invention relates to a device and a method for treating cancers and tumors with radiation.

BACKGROUND

Some cancers and neoplasms are easier to treat with radiation than others. Hard-to-reach neoplasms, such as those in the esophagus, intestines and other lumens, are often treated via Brachytherapy so as to minimize radiation to adjacent, healthy tissue.

Brachytherapy delivers radiation to small tissue volumes while limiting exposure of healthy tissue. In this regard, the delivered radiation conforms more to the target than any other form of radiation, (including proton therapy) as less normal transient tissue is treated. It features placement of radiation sources, such as small radioactive particles or needles, near or within the target tissue, thus having the advantage over External Beam Radiation Therapy (EBRT) of being more focalized and less damaging to surrounding healthy tissue.

Brachytherapy is a common treatment for esophageal, prostate, and other cancers. Approximately 15,000 and 480,000 cases of esophageal cancer are diagnosed in the U.S. and worldwide, respectively. At least 50 percent fail locally who present with curable cancers, which is to say that 50 percent suffer from persistence or recurrence of the cancers at the original cancer site.

Brachytherapy can be delivered in several rates: a Low-Dose Rate (LDR), a High-Dose Rate (HDR), and a very Low Dose Rate vLDR. The rates are expressed in Grays (Gy)/hour which are SI units of energy absorbed from ionizing radiation, equal to the absorption of one joule of radiation energy by one kilogram of matter. Since the inception of brachytherapy at the beginning of the 20th century (i.e., soon after the discovery of radiation) delivery has been predominately LDR.

LDR brachytherapy typically delivers radiation at a rate of about 50 cGy/hr (i.e., 0.5 Gy/hr) while HDR typically delivers at a rate of 5 Gy/min. The instantaneous rate is much higher at each dwell location for HDR brachytherapy as a very active source must traverse the various treatment locations during each treatment.

LDR brachytherapy delivers radiation continuously, while HDR brachytherapy delivers radiation intermittently over several days. Regardless of the dose rate, a total final dosage of 60 Gy or less is usually delivered to the patient during brachytherapy if it is the sole source of radiotherapy, and a total dose of 20-40 Gy is delivered during brachytherapy when used in combination with other forms of radiation treatment. These scenarios involve temporary implants in which the device is removed after completion of treatment.

Brachytherapy has been used to treat prostate cancer which has been practiced for more than half century. In this situation, very low activity material emitting a low energy is placed next to or within a tumor. Until now these low emitting devices have mostly been left in place permanently except in extraordinary circumstances. The most commonly employed LDR source is Iodine-125 ($^{125}$I) which decays at a low energy radiation of 30 keV and emits radiation at a dose rate of 0.4-1.0 Gy/hr (4 to 10 cGy/hr) for multiple days up to a nominal year. vLDR is commonly used for cancers in which the radiation source can be placed proximate to or in the neoplasm and left for a significant period of time or permanently, such as when radioactive material or seeds are placed in prostate tumors. vLDR sources are considered permanent implants but this invention provides an option for replacing the radioactive material while the physical carrier of the radiation source remains at the treatment site.

Clinicians administer HDR brachytherapy in multiple sessions to improve patient tolerance. Thus, the patient is subjected to the additional risk of multiple procedures, often requiring anesthesia. Patients with cancers within lumen, ducts, or tracts, such as cancer of the esophagus or biliary tract of the liver, have less tolerance for brachytherapy if connections (for example, catheters) are connected externally for multiple days, because of irritation and the risk of life-threatening infections.

HDR employs a primary housing containing a relatively high energy source (about 10 Ci), such as Iridium-192 (0.4 MeV). Treatment sessions last about 30 minutes. HDR is commonly applied in 2 to 3 daily sessions over the course of a few days, or multiple placement of an after-loading catheter in e.g. esophageal cancer treatment.

Brachytherapy dosage is usually calculated at a fixed distance from the radiation source. HDR requires a highly active source delivering radiation at a dose rate of about 12 to 20 Gy/hr. Hot and cold spots, due to uneven distribution of radiation does, occur with small deviations in distance between the tissue and the radiation source. Thus, brachytherapy treatment using a centralized radioactive material housing or containment can result in significant patient toxicity if the radioactive source is not centralized. For example, for patients with esophagus cancer, potentially life-threatening fistulas occurred at a rate of 12 percent when treated with HDR brachytherapy in the study of Gasper et al, *International Journal of Radiation Oncology, Biology, Physics* 38 (1) 127-321 (1997), the entirety of which is incorporated by reference. However, there are many reasons for the source to be skewed to one side as even an active tumor could displace the source. Lastly, HDR treatment requires a specially shielded patient room with appropriate radiation precautions.

State of the art devices for delivering radiation to internal tissues lack two important essential features: 1) the ability to remove or replace the radiation sources in situ when clinically appropriate, and 2) the ability to change the geometry, energy or radioactive sources of the radioactive particles or seeds in situ according to clinical needs. Typically, once the radiation source carrier and the radiation source is placed, they remain permanently within the patient. Leaving a permanent radiation source in a patient, where it or its carrier may migrate over time or the tumor may change in shape or size, has the undesirable effect that healthy tissue will be exposed to the radiation, while the target cancerous tissue is not. The ability to remove the radioactive sources in this situation or prior to surgery, while clinically useful, is currently lacking from the state of the art.

Additionally, it may be clinically necessary to continue radiation therapy after the activity of the radioactive material has decayed. For example, $^{125}$I has a half-life of about 60 days. If the tumor is still present or grows in size after an initial brachytherapy treatment (which sometimes occurs within six months), then it would be advantageous to replace the depleted radiation source with a source that has higher activity or shorter half-life. This is because faster growing tumors may be better controlled with radiation that has a shorter half-life or that decays and emits radiation faster.

Additionally, it would be advantageous to adjust the position and the activity of the radioactive source on its carrier in response to changes in tumor shape and size, carrier position, and other relevant therapeutic factors. It also may be appropriate to remove the radiation sources before surgery or other intervention to reduce personnel exposure or damage to sensitive equipment.

A need exists in the art for a device to deliver radiation and other medicaments to a patient at a lower total but more concentrated dose but with the beneficial effects of a higher dose. The device should facilitate the removable positioning of vLDR radiation sources in close spatial relation to the neoplasm or target tissue requiring treatment. The device should therefore feature a means for accommodating indefinite placement of the radiation source proximal to the target tissue, the means also allowing for removal or replacement of the radiation source, all with minimal invasive activity. The device should also allow the radioactive sources to be positioned in a preformed geometry that is customized to patient anatomy and the target tissue.

SUMMARY OF THE INVENTION

An object of this invention is to provide a system of brachytherapy that overcomes many of the disadvantages of the prior art.

Another object of the invention is to provide a device to enable focalized delivery of radiation in patients. A feature of this device is a medicament source supported by an expandable stent either attached to or within the structures. An advantage of the device is that the medicament may be removed or replaced according to clinical need. Another advantage of this device is that the medicament may be contained within tubular members and may be removed or replaced by relatively non-invasive means, such as by using endoscopic methods, all while the device remains in the patient.

Still another object of the instant invention is to provide a device comprising a radiation source removably attached to a support or within a tubular structure for brachytherapy applications. A feature of this device is that the radiation source is positioned on the periphery of an expandable stent near the target tissue, instead of positioned in the middle of the duct, tract or other endoluminal space. An advantage of the instant invention over the current practice of treating endoluminal spaces using a centralized catheter is that the distance between the radiation source and the target tissue is more consistent, and therefore has smaller and fewer deviations from the desired distance, when compared to a centralized radiation catheter. This allows for safer and more efficient delivery of radiation.

Yet another object of the invention is to provide a receiver for medicaments, wherein the receiver is inside a patient. A feature of the receiver is that it is adapted to removably receive radioisotopes, therapeutic materials, pharmaceuticals, drugs, diagnostic materials, biologically active compounds or materials, or any other medicament. An advantage of the invention is that the medicament may be applied locally in a focalized manner to target tissues. Another advantage is that the medicament receivers may be modified to facilitate diffusion or movement from the receivers to target tissue.

Another object of the invention is to provide a receiver for medicament for applications such as kyphoplasty. A feature of the invention is that the receiver is an expandable stent comprised of a hollow tubular member, and in one alternative embodiment the expandable stent is comprised of shape memory material. An advantage of the invention is that the stent is pre-formed to the desired three dimensional shape, providing a means for pre-forming the geometry and spatial relationship of radioactive particles and inert spacers subsequently contained therein and preserved after placement in a patient. This allows the radioactive sources to be positioned in a preformed geometry that is customized to patient anatomy and the target tissue.

The invention provides a medicament delivery vehicle, the vehicle comprising tubular members adapted to removably receive the medicament and an expandable stent adapted to receive the tubular members.

Also provided is a medicament delivery vehicle, the vehicle comprised of tubular members which receive the medicament wherein the medicament comprises discrete entities and each of said entities are removably positioned at predetermined regions within the members.

BRIEF DESCRIPTION OF THE DRAWINGS

The invention together with the above and other objects and advantages will be best understood from the following detailed description of the preferred embodiment of the invention shown in the accompanying drawings, wherein.

DETAILED DESCRIPTION OF THE INVENTION

Figure 1:
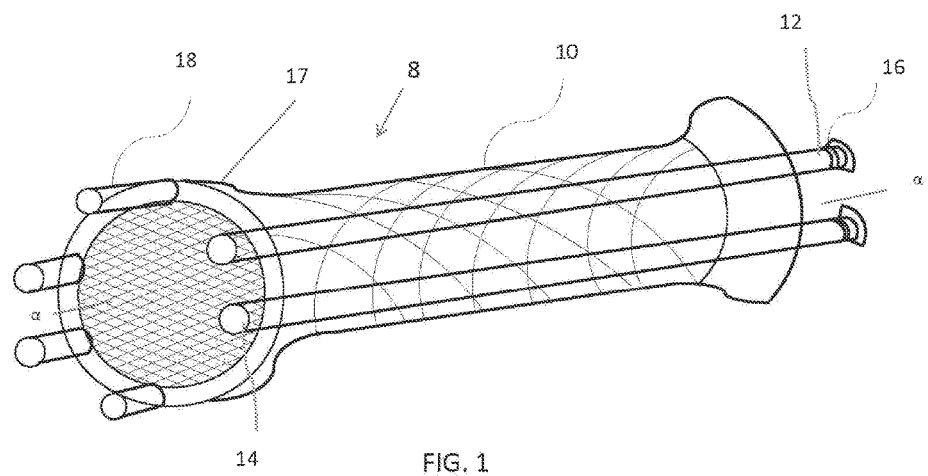
FIG. 1 is an elevational cutaway view of a medicament delivery vehicle, comprised of an expandable stent and tubular members, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides irradiated stents for cancer treatment, wherein the stents offer palliation and minimally interfere with chemotherapy, while potentially decreasing patient toxicity and the incidence of fistulas.

The invented device is envisioned for treatment of colorectal cancers, which have incidence rates of about 40,000 per year in the United States and 1.2 million worldwide. The proposed device also decreases bleeding perforations otherwise caused by sub-optimum placement of the device, thereby creating hotspots and fistulas to tissue.

The invented luminal stent device is suitable to treat pancreatic and biliary cancers, which occur at a rate of 50,000 per year in the United States and 280,000 worldwide. Specifically, the invented device and method will assist in relieving pain obstruction with the potential of prolonging survival among these patients. The inventor envisions 50 percent of these patients benefiting from the invented device and method.

Another application is the treatment of primary or metastatic liver cancers, which have incidence rates of about 100,000 in the United States and 1 million worldwide. These cancers are currently usually treated by radiofrequency ablation or cryosurgery. Adjuvant localized radiation as with an appropriately shaped device may help in the local tumor control. The device could be placed percutaneously through a needle.

Some other treatment applications are renal (40,000 cases/year in the United States and 250,000 worldwide), uterus-body (250,000/year worldwide), uterus-cervix (12,000 cases annually in the United States), breast (200,000/year in the United States and 1.4 million/year worldwide), and bladder (0.4 million/year worldwide) cancers.

Generally, the invented brachytherapy stent device has the potential to improve treatment for many cancers, by better preserving function, decreasing bleeding, providing palliation, and providing alternative treatments for applications in which currently surgery is the only available treatment.

The invention features a combination of brachytherapy and stents to provide effective radiation treatment. This combination provides all of the benefits of high dose radiation therapy with the safety and convenience associated with low dose therapy. For example, cancer treatment of the esophagus with stents provide immediate short term relief with an increase of Health-Related Quality of Life (HRQL) scores at one month. Simultaneously, brachytherapy improves HQRL scores and dysphagia symptoms 2-3 months after treatment. The example application of brachytherapy by use of radioactive particles is included in this description, but is not the only application to which the device is limited.

An embodiment of the invention comprises a medicament receiver arranged linearly along an expandable stent such that the receiver extends in parallel with the longitudinal axis of the receiver. (Heretofore, stents have been used primarily to re-expand an obstructed lumen, ducts, tracts, or other confined cavities. A stent provides a mechanical means of supporting luminal walls and opening ducts or other passageways. However, tumors often grow over or within stents, eventually occluding the lumen and embedding the stent within the tumor.)

The invention simultaneously allows for the receiver to contain medicament and the stent to expand. The receivers, which may be tubular in shape, are attached to the outside or inside of the stent walls, or embedded within the stent itself.

Aside from positioning radioactive particles in a plurality of linearly arranged tubes, other arrangements of the radiation sources can be utilized. Those arrangements include positioning medicament particles or seeds in a spiral configuration within a stent.

In an embodiment of the invention, the medicament is contained in the tubular members on the periphery of the stent, and is in close apposition to the target tissue. The stent may be comprised of a myriad of materials, including but not limited to such reversibly deformable substrates as nitinol, surgical steel wire, wire mesh, non-ferrous material such as polymer, or another expandable material. The stent is placed into various sites for desired therapeutic intervention. The stent may be comprised of radiopaque materials, or may be comprised of radiotransparent materials, depending upon the application and the need for visualization of the seeds A replaceable, removable system is provided such that the medicament is not permanently affixed to its carrier. This allows for follow-up or replacement of the radioactive particles with more active radioactive sources. Additionally, this system will allow the radiation to be delivered to different patient regions of different size. An embodiment of the invention comprises flexible or stretchable tubular members of suitable diameter (for example, surgical tubing) attached to an expandable stent. In an example embodiment the device would be comprised of tubular members woven into the mesh of an expandable stent. The expandable stent may be comprised of a wire mesh or other suitable material, which may be expanded within the lumen by a surgical or other technique. A method of stent insertion is to wrap the stent around a deflated balloon and then inflate the balloon within the target lumen, thereby expanding the stent in situ.

The invention provides focalized treatment of specific tissues, including but not limited to the liver, kidney, ductile tissue, and the spine. The invention is envisioned to deliver any medicament or therapeutic material, such as radioactive brachytherapy particles, drug solutions, or two-part resins, but is not limited to any specific medicament or class of therapeutic material.

The present invention features tubular members attached to a stent comprised of a shape-memory material, such as a shape memory alloy or polymer or plastic. Preshaped devices defining a myriad of geometries are suitable, including but not limited to, spirals, spheres, planes and other symmetric forms. Planar forms may be necessary to treat larger treatment volumes, such as post-surgical scenarios related to lung cancer, pelvic cancer, post meningioma and multiple treatment sites. Asymmetric forms are also suitable, such as where a spiral defines a frusto-conical shape (e.g., exhibiting a narrow diameter at one end and a larger diameter at a second end).

The tubular members are adapted to receive medicament. In contrast to a normal elastic material, the deformation of a shape-memory material leads to a stable temporary shape. For a normal elastic material, after release of the deforming external force, the material resumes its original shape. For some shape memory materials, however, resumption of the original shape may require an external trigger such as heat, as the second temporary shape can be energetically stable. The present invention may also be comprised only of a single hollow tubular stent made of shape memory material, wherein the medicament, for example radioactive particles and spacers, are placed inside the stent so as to physically, directly contact the interior of the stent. Radioactive material may be embedded in the inner stent, the latter of which is removed, repositioned and replaced as clinically indicated.

Another application involves tubular members residing within a stent, whereby the medicament such as radioactive material is embedded in the tubular members, and adapted to be repositioned, removed and replaced as clinically indicated.

A stent made of a shape memory material allows the material to be pre-programmed by thermal and/or mechanical manipulations prior to insertion such that the stent will "remember" a particular shape once inserted in situ. The stent is then deformed into a temporary shape for delivery, typically by encasing it in a retractable sheath. Once the stent is released from the sheath, the stent is triggered, either naturally at ambient temperature, or by a temperature change (such as at body temperature) to return to its pre-formed final shape. This occurs because the material has a "memory" of its permanent shape it is given during pre-treatment at the manufacturer.

The stent(s) may be inserted through a needle or trocar into the desired site. They may be loaded more easily with radioactive material and appropriate spacers when using a straightened needle.

Stent Material Detail

A myriad of reversibly deformable materials are used as the stent in the invention. For example, nickel-titanium alloy is suitable for its durability. The alloy is commercially available from a myriad of sources. For example, Nitinol™, an alloy composed of nickel and titanium, is available from NDC, Inc. (Fremont, Calif.). Nitinol's solid state transformation occurs by thermal or mechanical manipulations, in which the molecular crystal structure changes. At room temperature, the nitinol stent is soft and elastic, resulting from its crystal structure called martensite. The stent is easily deformed and crimped into the desired shape when it is in this phase. During pre-treatment of the stent at the manufacturer, the material is heated while held in its desired final shape (dictated by the clinician) above a transition temperature, ranging from 38 to 50° C. or higher. At that point, the material assumes a rigid crystal structure called austenite.

Upon cooling back to room temperature, the stent returns to the martensite phase, which is elastic and thus easily formed into a temporary shape suitable for insertion. However, upon heating above a second transition temperature, typically near or at body temperature, the stent transitions back into the austenite phase and the original permanent shape. The precise temperature at which this occurs can be adjusted within 1 or 2 degrees by varying the composition of the nitinol and other metallurgic constituents.

Nitinol stents also exhibit stress hysteresis, in that once deployed in the target lumen, they expand until they are constrained by the lumen walls (akin to contact inhibition in biological systems), but do not exert a large outward radial pressure after contacting the lumen wall. Nitinol stents strongly resist inward force after converting to austentite at body temperature, and thus are not easily compressed. Instead, the stent in this phase remains semi rigid or rigid so as to be resistant against inward pressure. Nitinol and other shape memory alloys (such as various plastics, metal tubing and polymers) are well suited for stent applications as they can be deformed up to 8%, which is more similar to biological tissue (~10% strain limit) These alloys also exhibit superelasticity, in that they recover their original shape after severe deformations.

These properties make nitinol and other shape memory alloys ideal for stent manufacture, and provide an excellent method of placement of brachytherapy particles or other medicament in precise locations near the walls of lumen. While currently most shape-memory stents are permanent, nitinol stents have also been designed which are removable, as disclosed in Jayant et al, 2012, *Surg. Endosc.* 26:1664-1669, the entirety of which is incorporated by reference. Thus, in an alternate embodiment of the current invention, the stent itself or an inner subsection of the stent is temporary, and the brachytherapy particles or other medicament can be removed or replaced by removal of the entire device.

Shape Memory Polymers

The stent in the instant invention may be composed of Shape Memory Polymers (SMPs). SMP stents have the advantages of large recoverable deformation (as high as 200% or more, compared to 8% for SMAs), low cost, and low density. SMPs are described in Lendlein, A and Kelch, S, "Shape-memory polymers." Angew. Chem. Int. Ed. 2002, 41, 2034-2057, the entirety of which is incorporated by reference.

SMPs are composed of a mixture of two different types of polymer chains, soft segments and hard segments. For example, a common SMP is comprised of urethane hard segments and polyether or polyester soft segments. Both the soft and hard polymer chains do not change their molecular conformation or cross-linking upon mechanical deformation, unless heated above a transition temperature. When the material is stretched or deformed below transition temperature and then the external force is released, it rebounds to its original conformation and the material resumes its original shape. However, if polymers are heated above their transition temperature, their molecules rotate around their bonds, change their conformations, and break their cross-linking bonds when external pressure is applied. The material becomes deformed such that it no longer elastically resumes its original shape.

The soft segments have a lower transition temperature, $T_{trans}$, than that of the hard segments, $T_{perm}$. The material is given its final, permanent shape upon heating above $T_{perm}$ and deforming it to its desired shape as specified by the clinician. Thus, both the soft and hard segments change their molecular conformations and positions relative to each other, such that the permanent shape is the energetically favorable state.

The material is then cooled below both transition temperatures to a working temperature (usually room temperature) while applying external force to maintain the desired permanent shape. When at working temperature, the material elastically rebounds back to the original permanent shape if subjected to deformation.

To make the material assume a second temporary shape the material is heated above the transition temperature of the soft segment, $T_{trans}$, but kept below the transition temperature of the hard segment, $T_{perm}$. External force is applied to deform the material into the second temporary shape. The soft segments change their conformation and position while the hard segments remain rigid and unaffected. After cooling the material below $T_{trans}$ back to the working temperature while holding the material in its temporary shape, the material then stays in this temporary shape. The stent can then be deformed, while returning to the second temporary shape after external force is released. After insertion of the stent while in this temporary shape, the temperature of the stent reaches body temperature, which is above $T_{trans}$ but below $T_{perm}$. The soft segments lose their conformation and cross-linked bonds while the hard segments maintain their conformation, position, and cross-linked bonds. Thus, the stent returns to the original permanent shape, driven by the conformation and structure of the hard segments.

SMPs also can undergo transformations by non-thermal mechanisms, such as upon exposure to radiation (such as light) or chemical-sensitive polymers. SMP stents are not as strong as SMA stents. However, they are advantageous for some applications because of their cost, customizability, and relatively large deformation capacity. An embodiment of the instant invention positions medicament particles in tubular members that are connected to stents comprised of shape memory materials. Alternatively, the medicament and optionally substrate interposed between medicament particles, may be placed within the hollow core of a tubular stent made of shape memory materials. Medicament structure can be either free flowing or connected by a spacer substrate so as to maintain the position of the medicament particles relative to each other in a geometry determined by the shape of the neoplasm or lumen being treated.

An exemplary embodiment will be described in reference to FIG. 1 as numeral 8. Flexible tubular members 12 are attached to an expandable stent 10. The tubular members 12 reversibly receive the medicament. They are attached to the stent on the outside or inside walls of the stent, or embedded within the stent itself. The tubular members are arranged parallel to each other and also parallel with a longitudinal axis a of the stent 10. A preferred embodiment comprises tubular members made of surgical tubing or other suitable material that are woven into the mesh of an expandable stent. The shape of the stent 10 and the position, spacing, and number of the tubular members may be determined according to clinical needs, for example by prior diagnostic imaging. The tubular members define artificial lumens of appropriate diameter and appropriate material, for example surgical plastic or nylon in the case of brachytherapy. In one embodiment, the tubes are permanently sealed in some manner at the distal end by heat, crimping, gluing, or the use of a permanent or removable cap 16. The artificiality of the lumens is not confined to non-biological substrate, inasmuch as 3-D printing of human tissue, to be readily absorbed over time, also is envisioned.

The proximal (i.e. loading) end 14 of the tubular members may be open or reversibly sealed by a removable cap and sealed after receiving the medicament, for example by replacing a resealable cap, crimping, heat application, or other means. The medicament may be loaded into the tubular members 12 prior to insertion of the stent, or may be loaded by surgical means in situ after stent placement (which already contains empty tubular members) in the patient. Medicament may be removed from the tubular members, or replaced at a later time using endoscopic methods or other means, without removing the stent 10 from the patient.

In an embodiment of the invention, the first or proximal ends 17 of the stent terminate in a plurality of feeder tubes 18, such that the tubes are arranged along the periphery of the stent to facilitate medicament loading and retrieval. Typically, the proximal end is the loading end inasmuch as it is nearest the excision of the patient whence positioned inside the patient. Optionally, the tubes may also receive substrates or other material connected to, in contact with, or otherwise associated with the medicament to allow access and physical manipulation of the medicament.

Furthermore, the tubular members 12 may be modified to receive liquid drugs, resins, gels, diagnostic materials, or other medicaments. Diffusion of other materials or solutions from the tubular receivers may be accomplished by making modifications, for example including slits in the tubular members or using permeable membranes as part of the receiver construction. The instant invention may also be comprised of a temporary stent attached to radioactive particles. The radioactive particles can thus be removed by removing and replacing the stent attached to the radioactive source.

Figure 2:
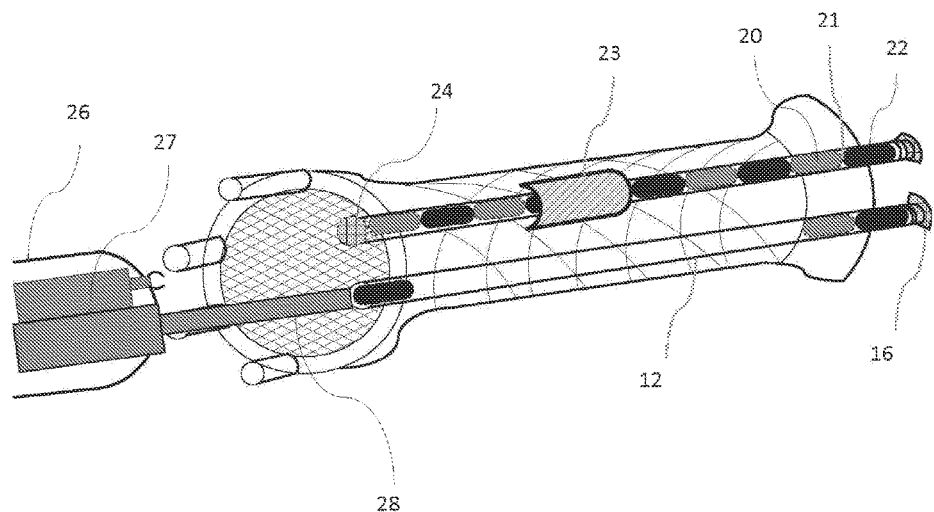
FIG. 2 is another elevational cutaway view of the medicament delivery vehicle, in accordance with features of the present invention.

FIG. 2 depicts an embodiment of the invention in instances where radioactive particles are contained in the tubular members for a brachytherapy application. FIG. 2 depicts an embodiment wherein the particles may be retrieved or replaced in situ using an endoscope equipped with requisite tools. Tubular members 22 may receive radioactive particles 20 comprised of isotopes such as currently available $^{125}$I, Ytterbium-169, Palladium-103, or Cesium-131.

$^{125}$I is a suitable source for vLDR applications, given its relatively short half-life (about 60 days) and relatively low energy (about 30 keV). Spacers 22 are comprised of inert material, and may maintain the desired geometry of the radioactive particles 20 relative to each other, and to the tissue being treated. The spacers may be free flowing, or attached to the particles flanking them, those flanking particles being radioactive particles, additional spacers or combinations thereof.

The diameter of the tubular members and the size of the particles contained therein will be constrained by the volume of the target lumen. As such, the diameter will be empirically determined upon receiving imaging data as to actual structural size of the effected tissue. Suitable radioactive particle sizes are those which can be loaded into the tubular members 22. Typical sizes have diameters beginning at about 0.4 mm and a length of about 4 mm (Iodine-125 "thin seeds" from GE/Oncura, or Ytterbium-169 particles from SPEC). Typical particle diameters and lengths range from about 0.8 to about 1.2 mm in diameter and 0.4 to 1.2 mm in length. Smaller size particles allow for easier placement of the instant invention in small-volume lumen, such as the biliary tract of the liver.

As noted supra, the particles and spacers may be connected via a substrate 21 or may be loose within the tubular member. In one embodiment, the substrate may be a thin linker made of a polymer or other suitable material that connects adjacent particles and spacers. In another embodiment, the substrate may be an adhesive, resin, or other material which binds adjacent particles and spacers together. In another embodiment, there may be a continuous substrate contained within the tubular member that extends along a longitudinal region of the tubular member, with the particles and spacers embedded within the substrate. In this embodiment, the substrate and embedded materials may then slide out of the tubular member.

An endoscope 26 can be used to load or replace the radioactive particles in situ by delivering the radioactive particles through a delivery catheter or loading tool 28. The endoscope may also include various capping- or sealing-tools 27 for the purpose of removing and replacing the cap during loading, or a tool for cutting the accessible end of the tubular member prior to loading and resealing (by mechanical crimping, heating, end rolling, and a combination of these means) the tubular member after loading. The capping tool may also be comprised of multiple devices, for example one tool for cutting and another for resealing. The endoscope 26 is also used to deliver other medicaments such as drug solutions by use of a delivery catheter or loading tool.

The radioactive particles may be removed or replaced according to therapeutic need. For example, the tumor may shrink or change its shape or the stent's position may migrate in situ. The position of the radioactive particles relative to the target tissue can be adjusted by changing the order and position of the spacers 22 and radioactive particles 20 in situ at a later time after stent insertion. Alternatively, if the stent comprises ferrous material, the stent may be manipulated by an externally applied magnetic field.

Shielding material 23 (such as tungsten) may be included as part of the tubular member 12 to prevent radiation exposure of undesired tissue. Tungsten is commonly used with Iodine 125. In one embodiment, the shielding material 23 may be attached to the tubular member. In other embodiments, the shielding material may be attached to one side of the radioactive substrates 20, or attached to or embedded in the stent itself 10. This shielding material may be used to prevent exposure of healthy or other tissue in which it is not desirable to expose the tissue to radiation. In one shielding protocol, the tubular member may be rotated about its axis so as to direct radiation from its encased particles in a predetermined direction.

The instant invention may comprise modifications to facilitate the placement and removal of medicament particles. In one possible embodiment, brachytherapy particles and spacers may be coated, for example with wax or silicone, to allow easier translocation into and out of the tubular members. In another embodiment, the spacers may be comprised of ball bearings that facilitate the movement of spacers and particles within the tubular members. In another embodiment the inside surface of the tubular members may be coated, for example with silicone or wax, to facilitate the movement of spacers and particles within the tubular members. In another embodiment, the tubular members may be comprised of ball bearings that are included within the tubular members. In another embodiment, the tubular members may be reinforced with additional elements to maintain their shape, keep the hollow center open, or prevent crimping of the tubular members upon deformations of the stent and attached tubular members.

Figure 3:
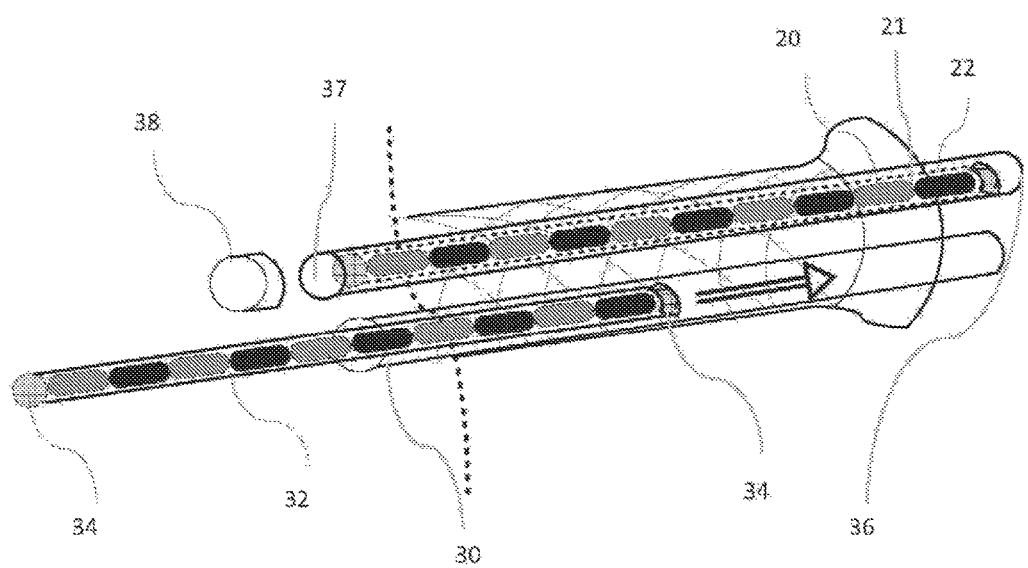
FIG. 3 is a schematic view of a medicament delivery device comprising a larger diameter outer sleeve and a smaller diameter inner sleeve slidably received by the outer sleeve, in accordance with features of the present invention.

FIG. 3 depicts an alternative configuration and loading method of radioactive particles and spacers in the tubular members. The tubular members may receive any medicament or therapeutic material, but as an example embodiment a medicament comprised of radioactive particles and spacers is depicted in FIG. 3. In this embodiment, the tubular member is comprised of a larger diameter outer sleeve 30 and a smaller diameter inner sleeve 32 that is slideably received by the outer sleeve. The outer sleeve 30 is attached along a longitudinally extending region of its outer surface to the stent. The outer sleeve is permanently sealed at one end 36 by the use of a permanent cap, crimping, glue, adhesive, or other means. Alternatively, the outer sleeve is reversibly sealed at the one end 36 via a male-female threaded configuration, a snap fit arrangement, hook and pile arrangement, or a tongue and groove arrangement or other arrangement as clinically indicated.

The outer sleeve is sealed at the loading end 37 by means of a replaceable cap 38 or by crimping or sealing or by other means in a manner that allows the end to be opened later, for example by using a cutting tool on an endoscope. The inner sleeve 32 and or catheters may contain the radioactive particles 20 and spacers 22, which may or may not be linked by a substrate 21. The radioactive particles can be removed at a later time by cutting the accessible end of the tubular member and retrieving the linked particles (that is, "wire stripping"), after which the particles can be replaced and the accessible end of the tubular member resealed.

The inner sleeve 32 is loaded with the radioactive particles and spacers prior to placement in the outer sleeve, and is sealed at both of its ends 34. Either prior to stent placement, or after stent placement, the sealed inner sleeve(s) (or plurality of catheters) is loaded into the loading end of the outer sleeve 37. As determined by therapeutic need, the inner sleeve can be removed or replaced in situ as needed at a later time. This may be accomplished by using an endoscope with the necessary tools or other surgical methods to open the outer sleeve loading end 37 by removing a replaceable cap 38, cutting the sealed end, or by other means. The inner sleeve 32 may then be removed, and a new inner sleeve pre-loaded with radioactive particles and spacers (or the original inner sleeve that was unsealed at its end 34 and the contents replaced) can then be inserted into the outer sleeve loading end 37. The outer sleeve loading end 37 can then be resealed by replacing the cap 38, by crimping, or by other means. The outer sleeve loading end 37 may be perforated or otherwise modified to facilitate cutting or other method of unsealing the end.

The outer sleeve 30 and inner sleeve 32 may be modified to receive liquid drugs, resins, gels, radionuclides or contrast agents used for imaging, biologically active compounds, or other desired material. Diffusion of materials or solutions from the tubular receivers may be accomplished by making modifications to either or both the inner and outer sleeves, for example including slits in the sleeves or using permeable membranes as part of the sleeve construction.

Figure 4A:
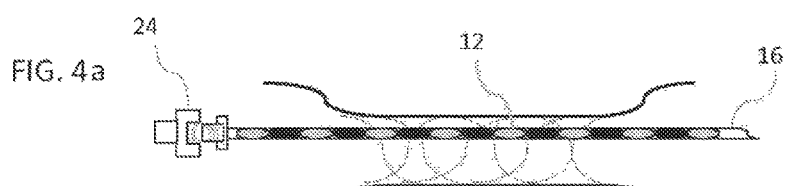
FIG. 4a depicts a medicament delivery device wherein tubular members are attached to the stent so that the tubular member is in direct contact with the stent and holds the medicament directly, in accordance with features of the present invention.

FIG. 4 depicts a comparison of the two designs of tubular members and loading methods. In one embodiment depicted in FIG. 4a, tubular members 12 are attached to the stent so that the tubular member is in direct contact with the stent. This tubular member holds the medicament directly. One end is permanently sealed by use of a cap, crimping 16, or other means. The medicament is loaded into the tubular member on the other end by removing a cap 24 or by opening the end by other means, for example by cutting the tube.

Figure 4B:
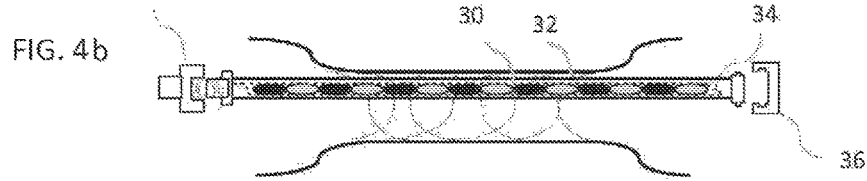
FIG. 4b depicts a medicament delivery device wherein outer sleeves of the tubular members are attached to the stent, while inner sleeves are of a smaller diameter such that they may be placed inside the outer sleeve. In this example embodiment, the inner sleeves hold the medicament directly, in accordance with features of the present invention.

In a second embodiment depicted in FIG. 4b, it is envisioned that an outer sleeve of the tubular members 30 are attached to the stent, while the inner sleeve containing loaded catheters is of a smaller diameter such that it can be placed inside the outer sleeve. In this embodiment, one end of the outer sleeve is permanently sealed, for example by use of a permanent cap 36. The other end is sealed by use of a removable cap 38 or is crimped and can be reopened by cutting, or sealed in some other way that allows for the end to be reopened after stent placement. The medicament is placed inside the inner sleeve 32, which is sealed at both ends, for example by crimping. The entire inner sleeve may be removed or replaced by use of an endoscope or other surgical means, according to clinical need.

Medicament Detail

The instant invention is not limited to the use of radioactive particles. Liquid solutions, pharmaceuticals including radiopharma-ceuticals, dissolvable solids, capsules containing liquid drugs, or other desired material may be included within the tubular receivers. These medicament particles or materials may also be separated by spacers to provide and maintain the geometry of the medicament along the longitudinal axis of the tubular receivers according to clinical need. For example, if a drug solution is to be applied to a desired portion of the tissue, then a drug delivery particle may be localized to this region by inclusion of spacers for the remaining length of the tubular receivers. In this embodiment, medicament particles may be loaded, removed, and replaced by surgical or other methods prior to or after stent placement.

The term medicament need not be restricted to therapeutic materials, but also materials for other clinical purposes. For example, the tubular members may comprise radiopaque substrates that allow for diagnostic imaging of the location of the tubular members or patient anatomy. Specifically, the instant device may be modified to deliver medicaments such as radiopharmaceuticals, radiotracers, or contrast agents for possible applications such as Computed Tomography (CT), Single Photon Emission Computed Tomography (SPECT), or Magnetic Resonance Imaging (MRI). A focalized application of such medicaments may be desirable for diagnostic imaging or other clinical applications because the substance may be at a desired local concentration without unnecessary exposure of non-target areas as occurs with systemic administration.

Other medicaments that may be used with the instant device include but are not limited to small interfering RNA (siRNA), DNA used for gene therapy, monoclonal antibodies targeted to relevant receptors, growth factors such as the Insulin-like Growth Factors (IGFs), radiolabeled nanoparticles, or medicaments which are chemically targeted to desired tissues or areas.

The tubular members may also be modified to contain or be attached to instrumentation, such as capsules which contain a battery source, wireless transmitters, and instrumentation for acquiring diagnostic data. Diagnostic capsules are currently used for monitoring relevant physiological parameters, such as luminal pH, temperature, and pressure. An embodiment of the instant invention may be to include such devices within or connected to the tubular members of the stent. If such devices needed to be removed, replaced, or have their position along the tubular member adjusted, then endoscopic or other surgical methods may be used to do so.

Alternatively, a wireless-controlled capsule with self-locomotion abilities may be included in the instant device. Such a capsule or similar device may be modified to translocate along the length of a tubular member. An envisioned alternate embodiment would manipulate the position of medicament particles using this capsule or similar device, thus alleviating the need for invasive surgical procedures.

Figure 5:
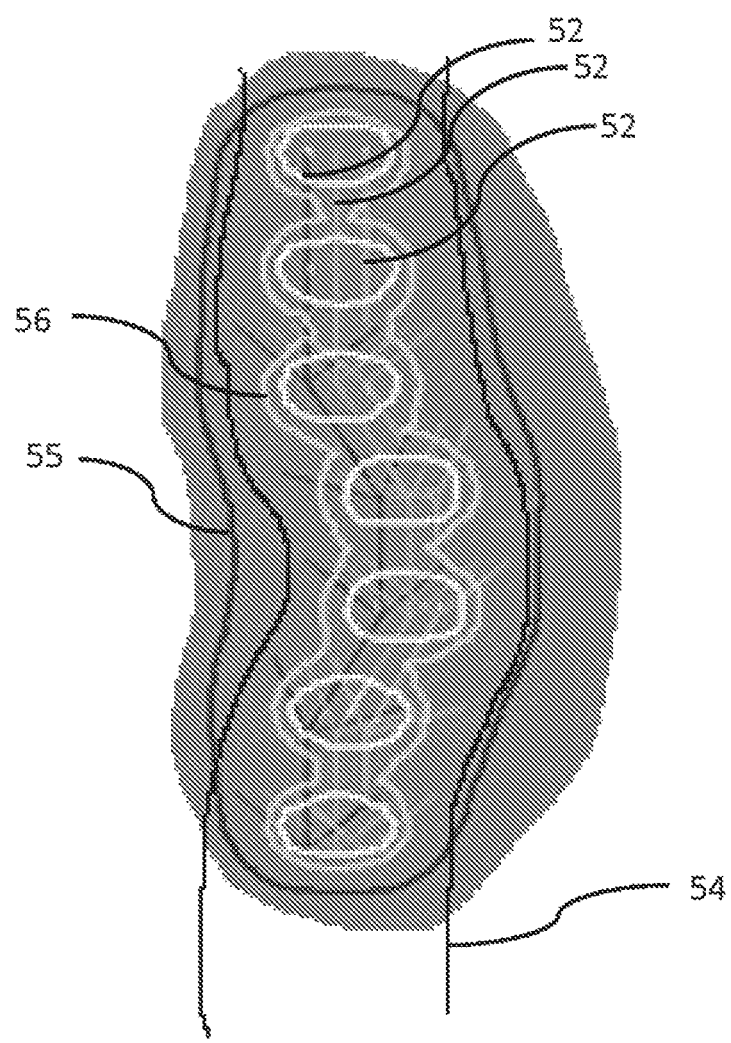
FIG. 5 is a schematic depiction of the distribution of the radiation intensity for a radiation delivery device wherein tubular members are attached to a stent placed within an esophagus, in accordance with features of the present invention.

FIG. 5 schematically depicts the use of the instant invention for vLDR brachytherapy of the esophagus. The tubular members 52 of the instant invention containing radioactive material follow the curvature of the esophageal wall 54. As a result, the distribution of radiation dosage at 100 percent 55 and at 200 percent 56 follows the curvature of the esophageal wall as well.

The current invention avoids "hot spots" (and the related patient toxicity, such as fistulas) caused by HDR therapy wherein a highly active source is included in a centralized catheter. For a centralized catheter, there are locations wherein the catheter is much closer to the wall, such that dangerously high levels of tissue irradiation causes patient toxicity, such as fistulas. Brachytherapy treatment using a centralized catheter for esophageal cancer results in significant patient toxicity, with a 12 percent occurrence of fistulas. For example, for Iridium 192, a common HDR source, a decrease in distance between the tissue and the radiation source from 10 cm to 5 cm results in an increased radiation dosage of 272 percent.

The present invention prevents hotspots by maintaining a more consistent distance between the radiation source and the tissue wall. Thus, the invention enables an LDR source attached to a stent, where the radiation source is held on the periphery of a stent to conform to anatomical curvatures. Thus, large deviations in distance between the tissue and the radiation source do not occur as they do for HDR centralized catheter treatment. Additionally, tumors of longer length can be treated with a vLDR source attached to a stent. If hot spots are unavoidable because of geometry, the modularity of the device allows placement of the hot spots within a tumor. The stent could also be modified to be utilized in HDR applications which typically require a larger stent internal diameter of the afterloading catheters.

Figure 6:
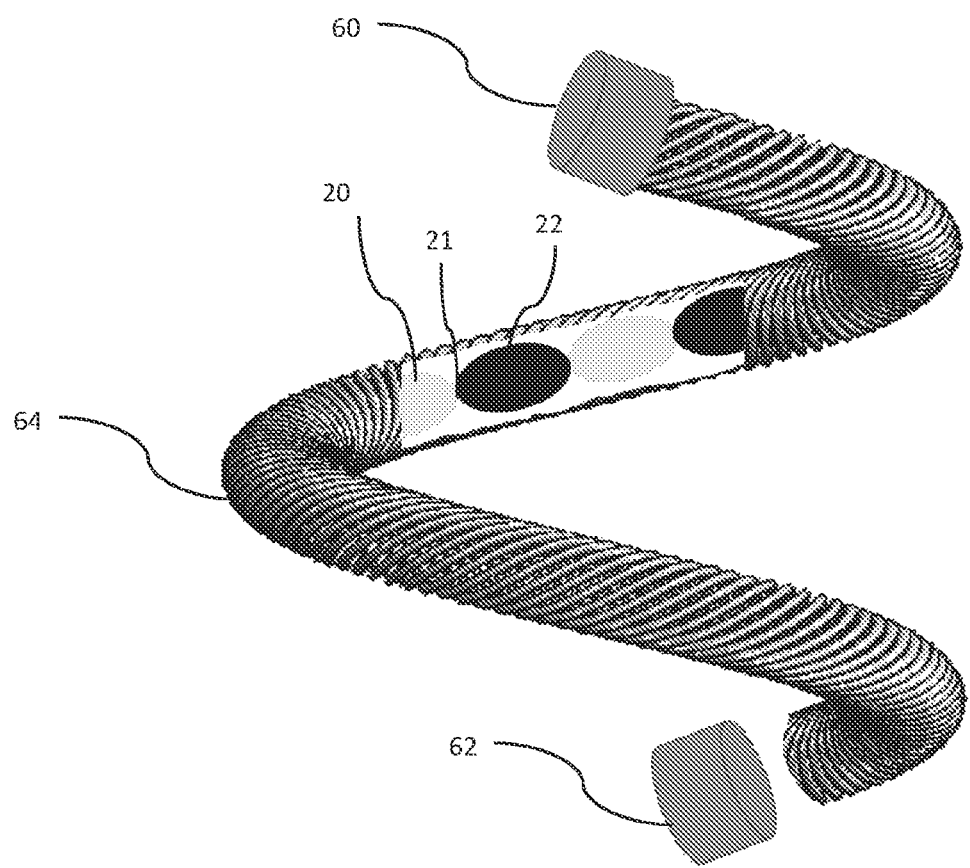
FIG. 6 depicts a medicament delivery device comprising a hollow tubular expandable stent wherein the medicament is placed inside the hollow center of the stent, in accordance with features of the present invention.

FIG. 6 depicts an alternate embodiment comprising a hollow tubular expandable stent wherein the medicament is placed inside the hollow center of the stent. In the case of a stent made of shape-memory materials, the stent is preprogrammed to a desired final shape so determined by visualization via MRI, endoscopy or a combination of these, and thus will expand after insertion into the desired shape.

While the embodiment in FIG. 6 is a helix, the stent may be of any shape. The distal (i.e., the stent end furthest from the cannula or other patient opening) end 60 is permanently sealed by means of a cap or other method, and the proximal accessible end 62 is either permanently or temporarily sealed. Medicament, including but not limited to radioactive particles 20 and spacers 22, which may be connected by a substrate 21, may be placed inside the tubular hollow stent so as to make direct physical contact with the interior surfaces of the stent. The accessible end 62 may be temporarily sealed by use of a removeable cap or other method, and thus the medicament may be reloaded and replaced at a later time.

Additional tubular members may be attached to the stent itself to receive the medicament, allowing for the medicament to be removed or replaced if required. In an embodiment, the medicament can be contained in an inner sleeve of the stent, and the inner sleeve with the medicament may then be placed into the hollow center of the stent or attached tubular members. This may then be removed at a later time from the accessible end if available 62 and may be replaced according to clinical need.

Another embodiment of the invention comprises an inner replaceable stent contained either in part or in whole within an outer stent, wherein the radioactive material is connected to, attached to, or embedded within the inner stent, and this inner stent is removed and replaced according to clinical requirements. The inner stent may be connected to the outer stent by means of button connectors which can be unfastened and fastened in situ. The inner stent may be attached to, tethered to, or in some other way associated with the outer stent such that its position is maintained by this association, while allowing the inner stent and outer stent to be dissociated and re-associated in situ.

Figure 7:
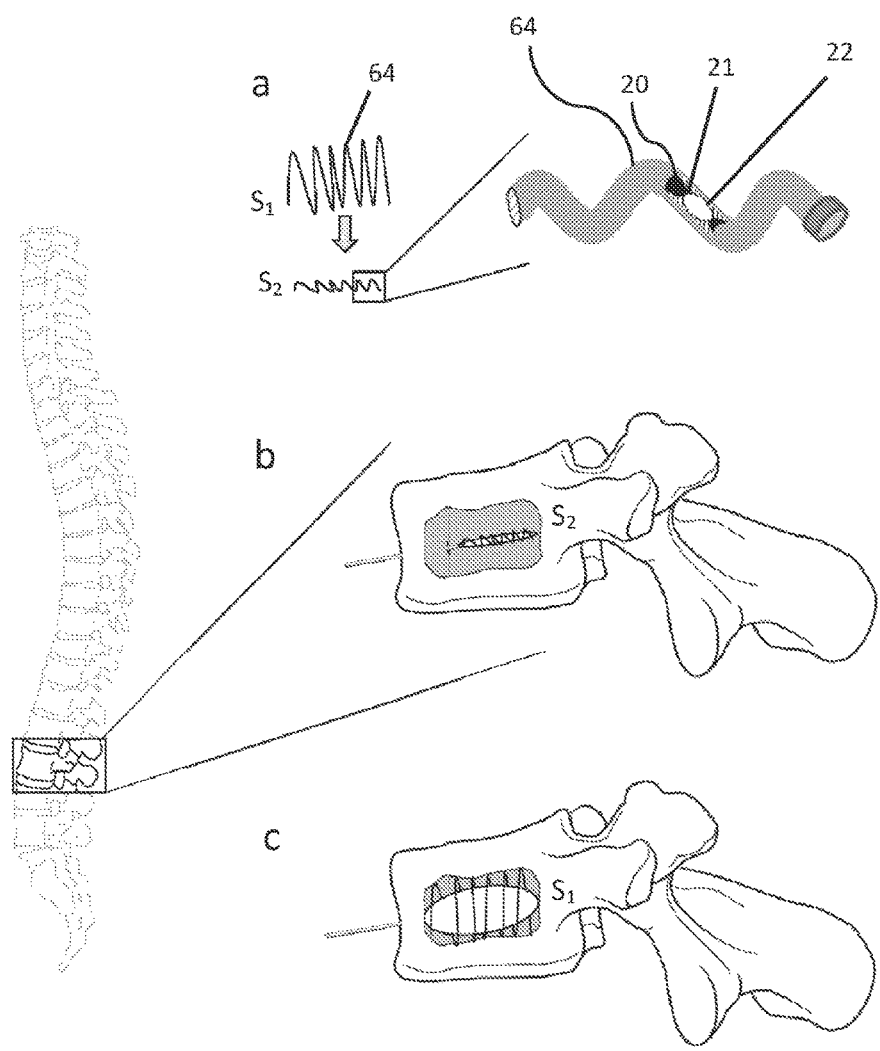
FIG. 7 depicts an example application of the instant invention to kyphoplasty, wherein the stent is wrapped around a deflated balloon which is then inflated within a collapsed vertebral body and then deflated and removed to leave a cavity within the body. The cavity is first filled with an appropriately shaped device and then filled with bone cement, in accordance with features of the present invention.

FIG. 7 depicts an example application of the instant invention to kyphoplasty. Kyphoplasty is often used to treat partially or completely collapsed vertebrate, or vertebral bone metastasis which occurs in 10-40 percent of patients with cancer. Kyphoplasty is used to provide structural support to the affected vertebrate, and typically involves inflating a small balloon in the vertebrate to create a cavity which is then filled with bone cement. The shaped device could be a spiral spheroid or other geometric shape. A follow up of this prototype could occur but not limited to other sites such as liver metastasis after focal tumorcidal therapy such as radio frequency ablation, cryosurgery, and radiosurgery. Other applications differing mainly on geometric details could include similar treatment for liver tumors, brain tumors, breast cancer and bladder cancer, multiple metastasis and other situations. In the latter situation the only alternative seems to be cystectomy.

The desired final shape of the medicament carrier (depicted as $S_1$ in FIG. 7a) is determined by the clinician prior to the procedure by imaging or other methods. The shape-memory stent 64 is pre-formed to "remember" the shape $S_1$. The stent is also pre-loaded with radioactive particles 20, spacers 22, which may or may not be associated with a substrate 21.

In an embodiment of the invented treatment protocol, the stent is deformed into a temporary shape while wrapped around a deflated balloon, depicted as $S_2$ in FIG. 7a. Alternatively the stent already defines a preformed shape. A cavity is created within the vertebrate by ablating or removing the tissue according to clinical need. The clinicians access natural apertures in the vertebrate or create apertures in the vertebrae (for example in the regions of the pedicles) using a large bone needle. The stent in the temporary shape $S_2$ and deflated balloon are then inserted through this hole into the vertebral cavity, depicted in FIG. 7b.

The balloon is then inflated to allow the vertebra to expand to its somewhat natural configuration prior to disease. The inflation also provides a means for the stent to assume its permanent shape $S_1$ within the target lumen, depicted in FIG. 7c. Additional thermal, mechanical, or other manipulations may be required to achieve the final configuration $S_2$.

The stent is then filled with bone cement or other material, permanently affixing the stent and radioactive sources within the cavity. A dummy preshaped device that is fully retrievable (i.e., connected to a rod) may be employed. A plurality of dummy tools provide a means to calibrate and therefore select which permanent device to apply in kyphoplasty-type scenarios. In operation, a guide sleeve (such as a trocar) is first inserted in a patient. The size of the sleeve is selected so as be adapted to slidably receive the dummy device. A suitable sleeve size may be a 14 G trocar.

After using a series of dummy devices to determine the dimensions of the resting place for the medicament delivery vehicle (such as spiral-shaped nitinol), the delivery vehicle is inserted into the resting place. To expand or spread out the now positioned delivery vehicle (which may or may not have shape memory), a balloon could be passed through the trocar to be positioned within the delivery vehicle, and then inflated. A second rod could be introduced within the same trocar, or an adjacent trocar to provide a means for adjusting the positioning of the device within the resting place.

The invention provides a system of treating the metastasis site but without exposing healthy surrounding tissue with permanently embedded radiation sources. In this embodiment, a radiation source is attached to or placed within a stent which is expanded against the lumen wall, wherein the geometry of the radioactive particles is determined and preserved by separation of the particles with spacers. This would allow for particle position to be customized to maximize delivery to the tumor and minimize exposure to healthy tissue.

Three dimensional configurations of a tumor are ascertained by imaging and the precise position of loose or connected radioactive particles is calculated based on desired radioactive dosages in three-dimensional space. Details for such imaging are known and can be found in Langley et al, 2012, BJU International, 109, 1-6, the entirety of which is incorporated by reference. The use of these methods to determine particle position within tubular members positioned against the inner wall of a body cavity, such as a vertebral cavity during kyphoplasty, allows for a customized delivery of radiation, representing a significant improvement of delivery of radiation to tumors located on the wall of endoluminal spaces. Particle activity and position can be calculated based on information from imaging (such as X-ray or CT scans) or other means.

The invention provides a system whereby a removable vLDR radiation source is attached to a stent, wherein the radiation source can be left in the patient for longer periods, and can be removed or replaced if required. The ability to removably place vLDR radiation sources on the periphery of a stent would be advantageous over current HDR methods using a central catheter, as 1) the vLDR source would be held in direct apposition to the target tissue by the stent, 2) it could be left for an extended period of time in the patient, and 3) the radiation source could be removed and replaced according to clinical requirements, for example changes in tumor shape and size. Additionally, the presence of a vLDR source would improve the mechanical relief of dysphagia by the stent, as the vLDR would prevent the tumor from growing over the stent. The proposed device would allow for a removable vLDR radiation source that could be removed and replaced by relatively non-invasive surgical means, such as endoscopy.

The proposed device uses radioactive particles that are separated by spacers which may or may not be connected by substrates. The inclusion of spacers in the instant invention allows the geometry of the radioactive particles to be customized along the longitudinal axis of the stent, as spacers can be used to separate the desired position of the radioactive sources and allow therapeutic inventions to be localized to desired target tissue.

The present device may be modified to accept a HDR brachytherapy application. The indwelling tubes would be sized appropriately and the catheters would be of such length to extend outside the body where they would be attached to an HDR brachytherapy machine.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A stent, comprising:
   an expandable framework configured to be implanted and expanded within a body lumen to support a luminal wall;
   one or more tubular members positioned in a spiral configuration along an inner surface of the expandable framework;
   a plurality of radioactive particles positioned within the one or more tubular members;
   wherein the plurality of radioactive particles are designed to be removable from the one or more tubular members in situ.

2. The stent as recited in claim 1, wherein the expandable framework includes a mesh and wherein the tubular members are woven into the mesh of the expandable framework.

3. The stent as recited in claim 1, wherein the tubular members are encapsulated by the stent.

4. The stent as recited in claim 1, wherein the tubular members are partially embedded in the stent.

5. The stent as recited in claim 1, wherein the plurality of radioactive particles are in the form of radioactive seeds.

6. The stent as recited in claim 5, further comprising one or more non-radioactive spacers positioned between adjacent radioactive seeds in the tubular members.

7. The stent as recited in claim 1, wherein after the radioactive particles are removed from the tubular members, new radioactive particles may be inserted therein in situ.

8. The stent as recited in claim 1, wherein each of the tubular members is comprised of an outer sleeve attached to the expandable framework and an inner sleeve which fits inside the outer sleeve, wherein the radioactive particles are placed in the inner sleeve.

9. The stent as recited in claim 8, wherein the inner sleeves and the plurality of radioactive particles contained therein can be removed from the outer sleeves.

10. The stent as recited in claim 1, wherein the tubular members include slits, holes, or permeable membranes to allow release of the plurality of radioactive particles from the tubular members.

11. The stent as recited in claim 1, wherein a first end of the tubular members is sealed and a second end of the tubular members can be opened and closed in situ.

12. The stent as recited in claim 1, further comprising a shielding material to minimize exposure of radiation to non-targeted tissues.

13. A stent comprising:
    a tubular scaffold configured to be implanted and expanded within a body lumen to support a luminal wall;
    a plurality of radioactive seeds;
    one or more non-radioactive spacers; and
    one or more tubular members positioned along an inner surface of the tubular scaffold;
    wherein the tubular members receive both the radioactive seeds and the one or more non-radioactive spacers within the tubular members with the one or more non-radioactive spacers positioned between adjacent radioactive seeds to space the radioactive seeds apart within the tubular members, and wherein the radioactive seeds are positioned in a spiral configuration along the inner surface of the tubular scaffold.

14. The stent as recited in claim 13, wherein the tubular scaffold includes a mesh and the tubular members are woven into the mesh of the tubular scaffold.

15. A stent for implantation in a patient, comprising:
    an expandable tubular scaffold including a first end region, a second end region and a lumen extending therein; and
    a plurality of tubular members positioned along an inner surface of the tubular scaffold;
    a plurality of radioactive particles positioned with the plurality of tubular members;
    wherein the plurality of radioactive particles are designed to be removable from the plurality of tubular members in situ;
    wherein the tubular scaffold is configured to be expanded within a body lumen to support a luminal wall.

16. The stent of claim 15, wherein the tubular members are partially embedded in the tubular scaffold.

17. The stent of claim 15, wherein the first end region, the second end region, or both the first and second end regions include a flared portion, and wherein the plurality of tubular members extend into the flared portion.

18. The stent of claim 15, further comprising a plurality of removable sleeves slidably disposable into the plurality of tubular members, wherein each of the plurality of removable sleeves includes radioactive particles placed therein.

19. The stent of claim 15, wherein the plurality of tubular members are positioned in a spiral configuration along the inner surface of the tubular scaffold.

* * * * *